(12) United States Patent
Ikuta et al.

(10) Patent No.: US 8,420,115 B2
(45) Date of Patent: Apr. 16, 2013

(54) ORAL PREPARATIONS AND PROCESS FOR PRODUCTION THEREOF

(75) Inventors: Hiroshi Ikuta, Tokyo (JP); Toshio Yajima, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 1525 days.

(21) Appl. No.: 11/628,062

(22) PCT Filed: May 25, 2005

(86) PCT No.: PCT/JP2005/009509
§ 371 (c)(1),
(2), (4) Date: Nov. 30, 2006

(87) PCT Pub. No.: WO2005/117845
PCT Pub. Date: Dec. 15, 2005

(65) Prior Publication Data
US 2008/0031965 A1    Feb. 7, 2008

(30) Foreign Application Priority Data
Jun. 3, 2004 (JP) ................................ 2004-165654

(51) Int. Cl.
*A61K 9/10* (2006.01)
(52) U.S. Cl.
USPC ......................................... 424/439; 514/974
(58) Field of Classification Search .................. 424/439; 514/974
See application file for complete search history.

(56) References Cited

U.S. PATENT DOCUMENTS

| 5,599,556 A | 2/1997 | Meyer et al. |
| 5,972,373 A * | 10/1999 | Yajima et al. ................. 424/439 |
| 2001/0055619 A1 | 12/2001 | Petereit et al. |

FOREIGN PATENT DOCUMENTS

| CN | 1164424 A | 11/1997 |
| JP | 57-58631 A | 4/1982 |
| JP | 5-97664 A | 4/1993 |
| JP | 5-163163 A | 6/1993 |
| JP | 5-255075 A | 10/1993 |
| JP | 6-116138 A | 4/1994 |
| JP | 7-76517 A | 3/1995 |
| JP | 2518882 B2 | 5/1996 |
| JP | 2973751 B2 | 9/1999 |
| JP | 11-349473 A | 12/1999 |
| JP | 2000-169364 A | 6/2000 |
| JP | 2001-270821 A | 10/2001 |
| JP | 3247511 B2 | 11/2001 |
| JP | 3265680 B2 | 1/2002 |
| JP | 2003-119123 A | 4/2003 |
| WO | WO 88/02253 A1 | 4/1988 |
| WO | 93/17667 A1 | 9/1993 |
| WO | WO 00/18372 A1 | 4/2000 |

OTHER PUBLICATIONS

Office Action mailed Feb. 19, 2009 in Russian Patent Application No. 2006147222.
Office Action dated May 8, 2009 in Chinese Application No. 2005800180183.
Chen Ting, et al., "Coating process based on aqueous polymeric dispersion", Chinese Journal of Modern Applied Pharmacy, vol. 17, No. 5, China Academic Journal Electronic Publishing House, (Shanghai Institute of Pharmaceutial Industry, Shanghai 200437), pp. 339-342, Oct. 2000.
Hitoshi Hoshito, et al, "Iyakuhin Tenkazai Yoran", Kabushiki Kaisha Yakugyo Jihosha, Nov. 25, 1992, p. 42 to 43.
Supplementary European Search Report issued on Oct. 19, 2012 from the European Patent Office in a corresponding European Application No. 05 743 784.0.

* cited by examiner

*Primary Examiner* — Ali Soroush
(74) *Attorney, Agent, or Firm* — Sughrue Mion, PLLC

(57) ABSTRACT

Disclosed herein are oral preparations and their production process. The oral preparations are each composed of a complex and a coating composition applied on the complex. The complex has been obtained by dispersing or dissolving a drug having an unpleasant taste and a gastric high-molecular compound in a low melting-point substance heated to and molten at its melting point or higher and granulating the resulting mixture. The coating composition is composed of an insoluble high-molecular compound and a disintegrator at a weight ratio of from 80:20 to 99:1. In the form of microparticles or the like that contain the drug having the unpleasant taste, each oral preparation according to the present invention can maintain the masking of the unpleasant taste of the drug and the release profile of the drug even under acidic conditions.

3 Claims, No Drawings

ORAL PREPARATIONS AND PROCESS FOR PRODUCTION THEREOF

TECHNICAL FIELD

This invention relates to oral preparations and a process for producing the same, and specifically to oral preparations each excellent in the masking of a drug having an unpleasant taste and the control of its release profile and a process for producing the same.

BACKGROUND ART

With a view to masking a drug or the like having an unpleasant taste and controlling its release profile, numerous technologies have been reported to date for applying coating such as film coating to the drug.

For example, there has been reported a composition, which comprises layers of a drug such as ketoprofen provided on pellets formed of microgranules of an inert material and coating films of stearic acid and ethylcellulose or paraffin and a methacrylic acid copolymer provided on the layers of the drug, and which has sustained release properties over 4 to 22 hours or longer (Patent Document 1).

There has also been reported a dry syrup characterized by comprising coated particles obtained by applying coating films of any one of (a) stearic acid and a surfactant, (b) stearic acid, a surfactant, and a gastric polymer or enteric polymer and (c) a hydrogenated oil and a gastric polymer or enteric polymer onto spherical microparticles formed of a wax-like substance in which a readily water-soluble drug having an unpleasant taste is dispersed (Patent Document 2).

A taste-masking drug preparation comprising a coated powder or coated granule has also been reported. The coated powder or coated granule is characterized in that it comprises core particles, which contain a drug having an unpleasant taste, and coating films formed of a low melting-point substance and a low molecular-weight water-soluble substance and applied on the core particles (Patent Document 3).

A powder with a drug-containing, sustained-release preparation and a sweetener-containing placebo powder mixed therein has also been reported (Patent Document 4).

In the meantime, the present applicant has also reported technologies on microparticles or the like, which are formed of a low melting-point substance or the like with a drug, which has an unpleasant taste, and a gastric high-molecular compound dispersed or dissolved therein to mask the drug and to control its release profile (Patent Documents 5 to 7).

As one of preparation forms suitable for the administration of medicines to infants, dry syrups are known. A dry syrup is administered by suspending or dissolving it in water. When an infant is reluctant to take the dry syrup, it may be added to another drink which the infant likes, and may then be administered. The above-described microparticles or the like offer no problem when they are dissolved in water or the like and are then drunk. When taken in a form dissolved in an acidic drink such as a fruit juice drink, however, the drug contained in the microparticles may be immediately released, and due to its unpleasant taste, it may conversely become unpalatable.
Patent Document 1: JP-B-2518882
Patent Document 2: JP-B-3247511
Patent Document 3: JP-A-11-349473
Patent Document 4: JP-A-2001-270821
Patent Document 5: JP-B-3265680
Patent Document 6: JP-B-2973751
Patent Document 7: JP-A-2000-169364

DISCLOSURE OF THE INVENTION

The present invention, therefore, has as an object thereof the provision of a technology which can assure the masking of a drug in the above-mentioned microparticles or the like and its release profile even under acidic conditions.

The present inventors have proceeded with extensive research to achieve the above-described object. As a result, it has been found that by coating a complex, which has been obtained by dispersing or dissolving a drug having an unpleasant taste together with a gastric high-molecular compound in a low melting-point substance heated to or molten at its melting point or higher and granulating the resulting mixture, with a coating composition containing an insoluble high-molecular compound and a disintegrator at a particular weight ratio, the drug in the resultant oral preparation is not released to sufficiently achieve the masking of the unpleasant taste even under acidic conditions, leading to the completion of the present invention.

Specifically, the present invention provides an oral preparation comprising: a complex, which has been obtained by dispersing or dissolving a drug having an unpleasant taste and a gastric high-molecular compound in a low melting-point substance heated to and molten at a melting point thereof or higher and granulating the resulting mixture; and a coating composition comprising an insoluble high-molecular compound and a disintegrator at a weight ratio of from 80:20 to 99:1 and applied on the complex.

The present invention also provides a process for producing an oral preparation, which comprises: dispersing or dissolving a drug having an unpleasant taste and a gastric high-molecular compound in a low melting-point substance heated to and molten at a melting point thereof or higher, granulating the resulting mixture into a complex, coating the complex with a coating composition comprising an insoluble high-molecular compound and a disintegrator at a weight ratio of from 80:20 to 99:1, and then conducting curing at 35 to 45° C. to form a coating film on the complex.

The oral preparation according to the present invention is excellent in the masking of the unpleasant taste of the drug and its release profile even under acidic conditions.

Further, the coating composition employed in the process of the present invention for the production of the oral preparation has a low film-forming temperature, so that various low melting-point materials can each be used as a base for the complex in the oral preparation according to the present invention.

DETAILED DESCRIPTION OF THE PREFERRED EMBODIMENTS

The oral preparation according to the present invention is composed of a complex, which has been obtained by dispersing or dissolving a drug having an unpleasant taste and a gastric high-molecular compound in a low melting-point substance heated to and molten at a melting point thereof or higher and granulating the resulting mixture (hereinafter simply called "the complex"); and a coating composition comprising an insoluble high-molecular compound and a disintegrator at a weight ratio of from 80:20 to 99:1 (hereinafter called "the coating composition").

As the drug having the unpleasant taste in the present invention, no particular limitation is imposed insofar as an unpleasant taste is produced. Illustrative are macrolide antibiotics such as erythromycin, clarithromycin, kitasamycin, josamycin, midecamycin, roxithromycin and azithromycin; β-lactam antibiotics such as penicillin derivatives and cephalosporin derivatives; tetracycline antibiotics such as tetracycline; psychoneurotic drugs such as chlorpromazine and lithium carbonate; cardiotonics such as digitoxin; antipyretics such as sulpyrine; and antiulcer drugs such as cimetidine. Among these drugs having unpleasant tastes, the macrolide antibiotics, especially clarithromycin has an extreme level of unpleasant taste, so that the oral preparation according to the present invention is highly effective for clarithromycin. The amount of such a drug having an unpleasant taste to be mixed in the complex can be determined in accordance with the dose of the drug.

As the gastric high-molecular compound for use in the complex, a polymer having solubility in gastric juice can be mentioned. Illustrative are aminoalkylmethacrylate copolymer E, polyvinylacetal diethylaminoacetate (AEA), and mixtures thereof. These gastric high-molecular compounds are commercially available, for example, under the trade name of "EUDRAGIT E100" (product of Rohm Pharma GmbH). The amount of such a gastric high-molecular compound to be mixed in the complex can be from 1 to 60 wt. %, preferably from 2 to 40 wt. %.

The low melting-point substance used as a base for the complex can be such one that is usable as an additive to medicines and has a melting point of from 40 to 120° C., preferably 45 to 100° C. Such low melting-point substances can include hydrocarbons such as paraffin, microcrystalline wax and ceresin; oils or fats such as hydrogenated oils and cacao butter; fatty acids such as myristic acid, palmitic acid and stearic acid; higher alcohols such as cetanol and stearyl alcohol; polyhydric alcohols such as macrogol 6000 and macrogol 4000; waxes such as Japan tallow, carnauba wax and bees wax; fatty acid esters such as glycerin fatty acid esters, propylene glycol fatty acid esters, sorbitan fatty acid esters and sucrose fatty acid esters; and mixtures thereof. Among these low melting-point substances, preferred are glycerin fatty acid esters, stearyl alcohol, stearic acid, hydrogenated oils, macrogols such as macrogol 6000 and macrogol 4000, carnauba wax, paraffin, sucrose fatty acid esters, and mixtures thereof. The term "glycerin fatty acid ester" as used herein means a compound formed of glycerin and a fatty acid coupled together through one or more ester linkages, with a monoglyceride or triglyceride with one or three molecules of a fatty acid coupled to one molecule of glycerin being preferred. As ester-forming fatty acids, behenic acid, stearic acid, oleic acid, palmitic acid, myristic acid and lauric acid can be mentioned. The amount of such a low melting-point substance to be mixed in the complex is not specifically limited, but may preferably be from 2 to 98 wt. % or so.

It is preferred to produce the complex, for example, by spray congealing agglomeration to be described hereinafter. The use of spray congealing agglomeration for the production of the complex makes it possible to adequately mask the unpleasant taste of the drug and also to obtain the complex in a fine form and with excellent bioavailability.

Specifically, this production by spray congealing agglomeration can be conducted as will be described next. Firstly, the gastric high-molecular compound is dissolved or dispersed in the low melting-point substance which has been heated to and molten at its melting point or higher. In the resultant solution or dispersion, the drug having the unpleasant taste is dispersed. The thus-prepared dispersion is then subjected to spray congealing agglomeration under preset spray conditions to obtain the complex. The term "spray congealing agglomeration" as used herein is classified as one of granulation methods generally called "melt granulation methods", and is a method that liquid droplets formed by spraying a liquid or suspension are cooled to obtain spherical or granular solid particles. This method is characterized in that no organic solvent is used, and is different from spray drying, a typical example of the melt granulation methods, in that cooling is performed. The particle size of the complex produced by the spray congealing agglomeration may preferably be, but are not particularly limited to, from 10 to 1,000 μm, with 50 to 400 μm being particularly preferred.

The complex produced as described above is then coated with the coating composition. The insoluble high-molecular compound used in the coating composition is not soluble in an acidic solution, and for example, a pH non-dependent polymer such as ethylcellulose can be used.

Among these insoluble high-molecular compounds, aminoalkylmethacrylate copolymer RS is preferred. This is a copolymer of ethyl acrylate and ethyl methacrylate and chlorotrimethylammoniumethyl methacrylate, and is available on the market under the trade name of "EUDRAGIT RL30D" (product of Rohm Pharma GmbH) or the like.

On the other hand, the disintegrator used in the coating composition is one that hardly raises the viscosity of a liquid even when dissolved or dispersed therein. For example, starch, carboxymethylcellulose, low-substitution-degree hydroxypropylcellulose and the like are usable.

Among these disintegrators, carboxymethylcellulose sodium (CMC-Na) is preferred. It is available on the market under the trade name of "CELLOGEN PR-S" (product of Dai-ichi Kogyo Seiyaku Co., Ltd.) or the like.

The coating composition for use in the present invention can be obtained by mixing the above-described insoluble high-molecular compound and disintegrator such that their weight ratio becomes from 80:20 to 99:1, preferably from 90:10 to 97:3. At a curing temperature of from 35 to 45° C., preferably from 38 to 42° C., this coating composition hardens and forms films.

It is preferred to add a nonionic surfactant such as polysorbate 80 as a plasticizer to the coating composition. This nonionic surfactant can be added preferably in 10 to 30 wt. % or so to the coating composition.

Further, light anhydrous silicic acid or the like can also be added as an aggregation inhibitor to the coating composition. Its amount can be set preferably at 1 to 20 wt. % or so.

The production of the oral composition according to the present invention, which makes use of the complex and the coating composition, can be conducted, for example, as will be described next. Described specifically as an example, the complex granulated by spray congealing agglomeration as described can be coated with 0.1 to 2 g, preferably 0.5 to 1 g of the coating composition per gram of the complex, and curing can then be conducted at 35 to 45° C., preferably 38 to 42° C. to form coating films on the complex.

The above-described coating can be conducted, for example, under an inlet air temperature of 40° C. or so by using a coating apparatus such as a Wurster coating apparatus. On the other hand, the curing can be conducted for 5 to 50 hours or so by using a curing apparatus such as a tray dryer.

The oral preparation according to the present invention can be produced as described above. It is, however, preferred to treat surfaces of the coating composition with one or more inorganic compounds, which are selected from magnesium oxide, talc and light anhydrous silicic acid, after coating the complex with the coating composition but before the curing. By the treatment with such inorganic compound or compounds, the oral preparation is prevented from cohesion via the coating films after the curing, thereby making an improvement in productivity. In this case, it is preferred to evenly apply the inorganic compound or compounds onto the coating composition. The inorganic compound or compounds may be used in an amount of from 0.005 to 0.03 g or so per gram of the complex.

The oral preparation according to the present invention obtained as described above can be formulated into a granule, powder, capsules, tablets, a dry syrup or the like by a method known per se in the art either as it is or after mixing it with one or more of known additives, for example, excipients, disintegrators, binders, lubricants, antioxidants, coating agents, colorants, corrigents, surfactants, plasticizers, flavoring agents, etc. as needed. Among these preparations, the dry syrup is preferred in the present invention. This dry syrup has particularly preferred dispersibility in liquid.

EXAMPLES

The present invention will hereinafter be described in detail based on Examples and Test Examples, although the present invention shall by no means be limited to them.

Example 1

Production of Dry Syrup (1)

Clarithromycin (180 g), glyceryl monostearate (360 g) and "EUDRAGIT E100" (product of Rohm Pharma GmbH; 60 g) were molten and dispersed at 120° C., and were then subjected to spray congealing agglomeration by "Spray Dryer CL-12" (manufactured by Ohkawara Kakohki Co., Ltd.) to obtain a complex (particle size: 100 μm). Onto the complex (333 g), a coating formulation prepared from "EUDRAGIT RL30D" (product of Rohm Pharma GmbH; 600 g (solid content: 200 g)), CMC-Na (18 g), polysorbate 80 (72 g) and purified water (700 g) was coated using a Wurster coating apparatus "GLATT GPCG-1" (manufactured by Powrex Corporation). Light anhydrous silicic acid (10 g) was then added to and mixed with the thus-coated complex, followed by the curing at 40° C. for 10 hours in a tray dryer to obtain an oral preparation.

Using the oral preparation (316.5 g), corn starch (40 g) and D-mannitol (133.5 g) together with a binder solution obtained by dissolving hydroxypropylcellulose (10 g) in purified water (190 g), fluidized-bed granulation and drying was conducted in "FLUIDIZED-BED GRANULATION DRYER FLO-1" (manufactured by Freund Corporation) to obtain a 10% dry syrup.

Example 2

Production of Dry Syrup (2)

Clarithromycin (180 g), glyceryl monostearate (360 g) and "EUDRAGIT E100" (product of Rohm Pharma GmbH; 60 g) were molten and dispersed at 120° C., and were then subjected to spray congealing agglomeration by "Spray Dryer CL-12" (manufactured by Ohkawara Kakohki Co., Ltd.) to obtain a complex (particle size: 120 μm). Onto the complex (333 g), a coating formulation prepared from "EUDRAGIT RL30D" (product of Rohm Pharma GmbH; 600 g (solid content: 200 g)), CMC-Na (18 g), polysorbate 80 (72 g) and purified water (700 g) was coated using a Wurster coating apparatus "GLATT GPCG-1" (manufactured by Powrex Corporation). Talc (10 g) was then added to and mixed with the thus-coated complex, followed by the curing at 40° C. for 10 hours in a tray dryer to obtain an oral preparation.

Using the oral preparation (316.5 g), corn starch (40 g) and D-mannitol (133.5 g) together with a binder solution obtained by dissolving hydroxypropylcellulose (10 g) in purified water (190 g), fluidized-bed granulation and drying was conducted in "FLUIDIZED-BED GRANULATION DRYER FLO-1" (manufactured by Freund Corporation) to obtain a 10% dry syrup.

Example 3

Production of Dry Syrup (3)

Clarithromycin (180 g), glyceryl monostearate (360 g) and "EUDRAGIT E100" (product of Rohm Pharma GmbH; 60 g) were molten and dispersed at 120° C., and were then subjected to spray congealing agglomeration by "Spray Dryer CL-12" (manufactured by Ohkawara Kakohki Co., Ltd.) to obtain a complex (particle size: 100 μm). Onto the complex (333 g), a coating formulation prepared from "EUDRAGIT RL30D" (product of Rohm Pharma GmbH; 600 g (solid content: 200 g)), CMC-Na (9 g), polysorbate 80 (72 g) and purified water (700 g) was coated using a Wurster coating apparatus "GLATT GPCG-1" (manufactured by Powrex Corporation). Magnesium oxide (10 g) was then added to and mixed with the thus-coated complex, followed by the curing at 40° C. for 10 hours in a tray dryer to obtain an oral preparation.

Using the oral preparation (312 g), corn starch (40 g) and D-mannitol (138 g) together with a binder solution obtained by dissolving hydroxypropylcellulose (10 g) in purified water (190 g), fluidized-bed granulation and drying was conducted in "FLUIDIZED-BED GRANULATION DRYER FLO-1" (manufactured by Freund Corporation) to obtain a 10% dry syrup.

Example 4

Production of Dry Syrup (4)

Clarithromycin (180 g), glyceryl monostearate (360 g) and "EUDRAGIT E100" (product of Rohm Pharma GmbH; 60 g) were molten and dispersed at 120° C., and were then subjected to spray congealing agglomeration by "Spray Dryer CL-12" (manufactured by Ohkawara Kakohki Co., Ltd.) to obtain a complex (particle size: 100 μm). Onto the complex (333 g), a coating formulation prepared from "EUDRAGIT RL30D" (product of Rohm Pharma GmbH; 480 g (solid content: 160 g)), CMC-Na (14 g), polysorbate 80 (58 g) and purified water (560 g) was coated using a Wurster coating apparatus "GLATT GPCG-1" (manufactured by Powrex Corporation). Light anhydrous silicic acid (10 g) was then added to and mixed with the thus-coated complex, followed by the curing at 40° C. for 10 hours in a tray dryer to obtain an oral preparation.

Using the oral preparation (287.5 g), corn starch (40 g) and D-mannitol (162.5 g) together with a binder solution obtained by dissolving hydroxypropylcellulose (10 g) in purified water (190 g), fluidized-bed granulation and drying was conducted in "FLUIDIZED-BED GRANULATION DRYER FLO-1" (manufactured by Freund Corporation) to obtain a 10% dry syrup.

Comparative Example 1

Production of Comparative Dry Syrup

Clarithromycin (180 g), glyceryl monostearate (360 g) and "EUDRAGIT E100" (product of Rohm Pharma GmbH; 60 g) were molten and dispersed at 120° C., and were then subjected to spray congealing agglomeration by "Spray Dryer CL-12" (manufactured by Ohkawara Kakohki Co., Ltd.) to obtain a complex (particle size: 100 μm). Using the complex (166.5 g), corn starch (65 g) and D-mannitol (258.5 g)

together with a binder solution obtained by dissolving hydroxypropylcellulose (10 g) in purified water (190 g), fluidized-bed granulation and drying was conducted in "FLUIDIZED-BED GRANULATION DRYER FLO-1" (manufactured by Freund Corporation) to obtain a 10% dry syrup.

Test Example 1

Organoleptic Bitterness Test

With respect to each of the preparations of Examples 1-4 and Comparative Example 1, an organoleptic bitterness test was performed as will be described hereinafter. Firstly, the preparation (1 g) was introduced into an aqueous solution of pH 4 (50 mL), followed by stirring with a spatula. Time was counted from the time of the introduction of the preparation. After 10, 60, 120, 180 and 240 seconds, about 2 mL samples were collected with pipettes, respectively. Each sample was introduced into the mouth and, after its taste was checked for several seconds, the sample was spit out and the mouth was rinsed with water to be ready for the checking of a taste of the next sample. Incidentally, the test solution was occasionally stirred with the spatula. An organoleptic assessment was performed in accordance with the following standards, and the results are shown in Table 1.

<Organoleptic assessment standards>

| (Assessment) | (Description) |
| --- | --- |
| A: | Not bitter. |
| B: | Not bitter, but the taste was modified. |
| C: | Bitter. |

TABLE 1

| | Time (sec) | | | | |
| --- | --- | --- | --- | --- | --- |
| | 10 | 60 | 120 | 180 | 240 |
| Ex. 1 | A | A | A | B | B |
| Ex. 2 | A | A | A | A | B |
| Ex. 3 | A | A | A | A | A |
| Ex. 4 | A | A | B | B | C |
| Comp. Ex. 1 | C | C | C | C | C |

Test Example 2

Dispersibility Test

With respect to each of the preparations of Example 1 and Comparative Example 1, a water dispersibility test was performed. The preparation (1 g) was introduced into water (50 mL), followed by continued stirring with a spatula. Time was counted from the time of the introduction. After 10, 20, 30 and 60 seconds, the dispersion state was visually determined. A dispersibility assessment was performed in accordance with the following standards, and its results are shown in Table 2.

<Dispersibility assessment standards>

| (Assessment) | (Description) |
| --- | --- |
| A: | Evenly dispersed. |
| B: | Not dispersed, but resulted in floating. |

TABLE 2

| | Time (sec) | | | |
| --- | --- | --- | --- | --- |
| | 10 | 20 | 30 | 60 |
| Ex. 1 | A | A | A | A |
| Comp. Ex. 1 | B | B | B | B |

INDUSTRIAL APPLICABILITY

The oral compositions according to the present invention can each maintain the masking of the unpleasant taste of the drug and the release profile of the drug even under acidic conditions, and therefore, can be widely used as excellent preparations not affected by drinking conditions.

The invention claimed is:

1. An oral preparation comprising: a complex having a particle size of 10 to 1,000 µm, which is obtained by dispersing or dissolving clarithromycin and aminoalkylmethacrylate copolymer E in molten glyceryl monostearate and granulating the resulting mixture; and a coating composition comprising aminoalkylmethacrylate copolymer RS and carboxymethylcellulose sodium at a weight ratio of from 80:20 to 99:1 and polysorbate 80 and applied on said complex to form a coating film on said complex through curing at 35 to 45 °C., wherein the surface of said coating composition is treated with at least one inorganic compound selected from the group consisting of magnesium oxide, talc and light anhydrous silicic acid prior to curing.

2. An oral preparation according to claim 1, which is a dry syrup.

3. A process for producing an oral preparation, which comprises:
dispersing or dissolving clarithromycin and aminoalkylmethacrylate copolymer E in molten glyceryl monostearate,
granulating the resulting mixture into a complex having a particle size of 10 to 1,000 µm,
coating said complex with a coating composition comprising aminoalkylmethacrylate copolymer RS and carboxymethylcellulose sodium at a weight ratio of from 80:20 to 99:1 and polysorbate 80, and
then conducting curing at 35 to 45° C. to form a coating film on said complex, and
treating the surface of said coating composition with at least one inorganic compound selected from the group consisting of magnesium oxide, talc and light anhydrous silicic acid prior to curing.

* * * * *